United States Patent [19]

Puritch et al.

[11] Patent Number: 4,983,591

[45] Date of Patent: * Jan. 8, 1991

[54] ENVIRONMENTALLY SAFE, BROAD SPECTRUM INSECTICIDE

[75] Inventors: George S. Puritch, Saanichton; Gregory S. Salloum; Willem W. Nijholt, both of Victoria, all of Canada

[73] Assignee: Safer, Ltd., Scarborough, Canada

[*] Notice: The portion of the term of this patent subsequent to Feb. 27, 2007 has been disclaimed.

[21] Appl. No.: 432,584

[22] Filed: Nov. 6, 1989

Related U.S. Application Data

[63] Continuation-in-part of Ser. No. 148,961, Jan. 27, 1988, Pat. No. 4,904,645.

[51] Int. Cl.$^5$ .................... A01N 37/00; A01N 43/54; A01N 47/10; A01N 57/00
[52] U.S. Cl. .................... 514/65; 514/66; 514/69; 514/74; 514/557; 514/558
[58] Field of Search .................. 514/65, 66, 69, 74, 514/557, 558

[56] References Cited

U.S. PATENT DOCUMENTS

| | | | |
|---|---|---|---|
| 1,773,102 | 8/1930 | Gnadinger | 514/72 |
| 2,071,484 | 2/1937 | Wittwer et al. | 514/70 |
| 2,346,256 | 4/1944 | Harvey | 514/72 |
| 2,374,918 | 5/1945 | Brown | 514/66 |
| 2,396,054 | 3/1946 | McKim | 514/70 |
| 2,396,983 | 3/1946 | Britton et al. | 514/70 |
| 2,421,223 | 5/1947 | Smith | 514/72 |
| 3,207,662 | 9/1965 | de Lisle | 514/70 |
| 3,560,613 | 2/1971 | Miskus et al. | 424/174 |
| 4,774,234 | 9/1988 | Puritch et al. | 514/86 |

FOREIGN PATENT DOCUMENTS 2919765 12/1965 Japan.

OTHER PUBLICATIONS

Roark, *Pyrethrum and Soap, A Chemically Incompatible Mixture*, 23 Journal of Economic Entomology 460.
Badertscher, *The Effect of Soap on the Toxicity of a Pyrethrum Product* Known as "Red Arrow," 24 Journal of Economic Entomology 268 Head, *Composition of Pyrethrum Extract and Analysis of Pyrethrins*.
Cory et al., *Insecticidal Values of Pyrethrum Soaps*.

*Primary Examiner*—Nathan M. Nutter
*Attorney, Agent, or Firm*—Lahive & Cockfield

[57] ABSTRACT

A combination of pyrethrum and fatty acid salt materials has been formulated which produces a stable, commercially useful, and environmentally safe pesticide. The specific composition comprises an aqueous solution having a pH within the range of 7.5 to 8.8; an aqueous solution comprising at least about 0.5 percent by weight of monocarboxylic acids and their alkali metal salts, where the acid mixture is at least 70% oleic acid and 6% linoleic acid; a pyrethrum extract; a solvent for the pyrethrum, which is preferably a 2-6 carbon alcohol; a trace amount of an antioxidant. The composition is effective against insects of at least the orders Homoptera, Coleoptera, Dermaptera, Hemiptera, and Lepidoptera, and against crustacea of the order Isopoda.

10 Claims, No Drawings

ENVIRONMENTALLY SAFE, BROAD SPECTRUM INSECTICIDE

REFERENCE TO RELATED APPLICATIONS

This application is a continuation-in-part of U.S. patent application Ser. No. 148,961, filed on Jan. 27, 1988, and now U.S. Pat. No. 4,904,645 and entitled "Environmentally Safe, Broad Spectrum Insecticide", the disclosure of which is incorporated herein by reference.

BACKGROUND OF THE INVENTION

This invention relates to an environmentally safe insecticide composition. More particularly, the invention features a specific insecticide formulation consisting of certain fatty acid soaps and pyrethrins together with a stabilizer and carrier, which formulation exhibits improved insecticidal properties as compared with the individual components, is effective in the control of a broad range of leaf eating and other insects, is environmentally safe, and has acceptably low phytotoxicity.

The use of insecticides has greatly enhanced agricultural productivity, but it has become apparent that there are limits to the amount of petrochemical-based materials that safely can be absorbed into the environment. Catastrophic, unanticipated, relatively long term effects experienced with materials such as DDT have increased awareness of the potentially dangerous environmental impact of widespread use of synthetics, contributed to the creation of regulatory agencies charged with protecting the environment, and promoted the development of potent, but apparently less dangerous insecticidal materials made from petrochemicals. These new insecticides are nevertheless far from ideal from the point of view of environmental safety, and sometimes collect in food and fresh water resources.

Recently, natural insecticidal materials such as bacterial preparations lethal to insects have been available commercially. However, the potential of non-bacterial, natural materials having insecticidal properties has largely been ignored, presumably because of the higher cost and lower insecticidal activity of such known natural substances.

Salts of fatty acids, primarily sodium or potassium fatty acid soaps, recently have been used commercially as an insecticide. Compositions having excellent insecticidal properties which exploit these salts are available commercially under the trademark SAFER INSECTICIDAL SOAP. This product accordingly constitutes an exception to the trend noted above. These fatty acid soaps are naturally occurring materials having no known long term environmental effects. They are very effective against mites and soft bodied insects such as aphids and whiteflies, but less effective against other types of insects.

Pyrethrum was used commercially many years ago as an insecticide, primarily in the form of "oleoresin of pyrethrum". Oleoresin of pyrethrum is an archaic pharmaceutical term for an ether extract of the cinerariaefolium variety of chrysanthemum. It contains volatile oils and components having insecticidal properties, called pyrethrins, jasmolins, and cinerins. These materials are known to be toxic to insects, essentially non-toxic to mammals, to lack persistence in the environment, and to be characterized by negligible biological magnification in the food chain.

One major problem with the use of these materials (hereinafter "pyrethrins") as insecticides is their high cost per unit dose. Attempts to extend the efficacy of the pyrethrins to provide economic feasibility have not been commercially successful. An example of such a composition comprising a mixture of saponified organic acids, i.e., salts of coconut oil, and pyrethrins was sold commercially under the trademark Red Arrow about 55 years ago. However, these mixtures did not solve the expense problem because of their high pyrethrin content, about 40% by weight, and because the coconut oil soaps contributed little to their insecticidal efficacy. In fact, most commercially available fatty acid soap compositions contain an excess of alkali which is thought to promotes hydrolysis and inactivation of pyrethrins. Pyrethrin-based insecticides also degrade rapidly in storage and in use.

Other materials which have been used to extend the efficacy of pyrethrins are toxic not only to insects but also to a variety of plants and animals. One material often suggested for use with pyrethrins is piperonyl butoxide. While this type of composition can produce a very potent insecticide, high doses can cause nausea in many animals including man, and the compositions are significantly phytotoxic. Other combinations of insecticides and pyrethrins have either presented similar toxicity concerns or loss of effectiveness due to inactivation of the pyrethrins.

It is an object of this invention to provide an insecticide formulation comprising natural, biodegradable materials which are inexpensive, non-toxic to a wide variety of plants and animals, and effective against a broad spectrum of insect life. Another object is to provide a specific, environmentally safe insecticidal combination of natural products which has a commercially acceptable shelf life, low, acceptable phytotoxicity, and low cost.

These and other objects and features of the invention will be apparent from the description and the claims which follow.

SUMMARY OF THE INVENTION

The present invention features a specific insecticidal solution comprising a combination of active, readily biodegradable insecticidal materials in specific weight ratios formulated to retain, and indeed, to enhance the insecticidal effectiveness of the individual insecticidal materials. The insecticide is economical to use, toxic to many different types of insect pests, and substantially non-toxic to other animals and plants.

The insecticidal formulation of the invention is based on the discovery that contrary to the general teachings of the prior art, a combination of pyrethrin and fatty acid salt materials can be formulated to produce a stable, commercially very useful, and environmentally safe insecticide that is effective to protect plants against a wide variety of insect and related pests.

Accordingly, the invention provides a readily biodegradeable, environmentally safe, storage stabilized, aqueous, insecticidal solution for application to decorative and crop plants. The solution is effective to control plant damage caused by many chewing and sucking insects. It consists essentially of an aqueous solution having a pH within the range of 7.5 and 8.8, preferably 8.0–8.5, and containing the following ingredients in the following relative parts by weight:

A. Between 10 and 50 parts of a mixture of monocarboxylic acids and their alkali metal, preferably potassium, salts. The monocarboxylic acids comprise at least 70 percent oleic acid and its alkali metal salt and at least 6 percent linoleic acid and its alkali metal salt. The remaining components of the carboxylic acid mixture, if any, comprises other monocarboxylic acids (or their salts) having less than 21 carbon atoms or other inert materials.

B. Between 0.05 and 5.6 parts of a pyrethrum extract comprising about 20 percent of a mixture of insecticidally active substances selected from the group consisting of pyrethrin I, pyrethrin II, cinerin I, cinerin II, jasmolin I and jasmolin II;

C. Between 15 and 225 parts of a low molecular weight alcohol. Preferably, the alcohol has 2–6 carbon atoms. Excellent results have been obtained with isopropyl alcohol and ethanol.

D. A trace amount of an antioxidant, preferably a hydroxylated aromatic material, and most preferably butylated hydroxytoluene.

The Composition is effective on application to a plant at a dilution in water such that the applied solution contains at least about 0.5 percent by weight of the monocarboxylic acid mixture and at least 0.005 percent of the mixture of insecticidally active pyrethrum extract substances. The composition provides protection against plant damage from infestation from insect species from at least the orders Homoptera, Coleoptera, Dermaptera, Hemiptera, and Lepidoptera, and from crustacea species from the order Isopoda. More specifically, application of the solutions is effective against species from the families Homoptera:Aphididae, Homoptera:Aleyrodidae, Homoptera:Coccidae, Homoptera:Psyllidae, Coleoptera:Chrysomelidae, Coleoptera:Tenebrionidae, Lepidoptera:Arctiidae, Lepidoptera:Lasiocampidae, Lepidoptera:Tortricidae, Lepidoptera:Pieridae, and Lepidoptera:Noctuidae. These orders and families include essentially all northern hemisphere insects which damage ornamental plants, trees, and food and other crops.

The insecticidal solutions also are effective in the control of mosquitoes, fleas, lice, and ticks, and accordingly may be used, for example, to protect pets and their resting places in the home.

The solution of the invention preferably is marketed as a concentrate wherein ingredient A is present at about 20 percent by weight and ingredient B is present at about 1.4 percent by weight. Preferably, ingredients A through D together comprise at least about 20 percent by weight of the concentrate. Dilution of the concentrate with water (20:1) produces a ready-to-use solution having the insecticidal properties noted above and comprising about 1.0 percent ingredient A and about 0.07 percent ingredient B (0.014 percent active pyrethrum extract components).

In addition, the solution of the present invention is marketed in a dilute, ready-to-use formulation having the same percentages of A and B as the dilute solution of the concentrate noted above. As marketed, ingredient C is present in an increased proporation to about 5.6 percent by weight to improve storage stability.

A third formulation of the solution of the present invention is marketed as a commercial concentrate wherein ingredient A is present at about 40 percent by weight, ingredient B is present at about 2.8 percent by weight, and ingredient C is present at about 30 percent by weight.

The insecticide of the invention is useful in protecting apples, avocados, grapefruits, lemons, oranges, tangerines, peaches, nectarines, apricots, pears, almonds, pecans, walnuts, kiwi fruit, blackberries, logan berries, raspberries, strawberries, and grapes, against insects including Japanese beetles, flea beetles, weevil adults, caterpillars, aphids, leaf hoppers, psyllids, scale crawlers, and sawfly larvae. In addition to commercial or vegetable garden protection, the insecticide of the invention can be used to protect lawns, turf grass, ornamental trees and shrubs, flowers, and house plants against a variety of insects. For example, the insecticide protects lawns against chinch bugs, lawn moth, sod webworm and army ants, and ornamental trees and shrubs against aphids, beetles, caterpillars, lace bugs, box elder bug, treehoppers, psyllids, sawflies, scales, and woolly aphids. Essentially complete insect protection is provided for ornamental trees and shrubs including azaleas, camellias, cacti, dogwood, rhododendrons, evergreens, and broad-leafed shade trees. The insecticide of the invention has been shown to provide effective protection for flowers including asters, carnations, chrysanthemums, geraniums, marigolds, petunias, and roses against attack by aphids, flea beetles, Japanese beetles, caterpillars, and whitefly.

DETAILED DESCRIPTION

The insecticide of the invention employs two insecticidally active materials: a pyrethrum extract; and a fatty acid soap of specific composition. The weight ratio of these two active components and the pH of the composition are important to the success of the invention. Significant deviations from the ratio result in rapid degradation of the important properties of the formulation. Specifically, the insecticidal efficacy and/or shelf and field stability are adversely affected progressively. Of the two active components, the pyrethrum is by far the more insecticidally potent on a weight basis. Thus, decreasing the pyrethrum extract content reduces the insecticidal efficacy and pest spectrum response until, at zero pyrethrum, the response is characteristic of the fatty acid component alone. Increasing the pyrethrum content, on the other hand, does not necessarily increase efficacy, as increasingly over time, the soap component tends to react with and reduce the efficacy of the pyrethrum extract. Lowering the solutions pH below about 7.5 progressively increases the phytotoxicity of the composition. Increasing the pH leads to pyrethrin degradation. The combination of components yields unexpected and synergistic insect kills on some species, i.e., a more effective kill rate as compared with the kill rate of the components individually.

The insecticide of the invention can be stored as a concentrate and then diluted for use, or may be kept in a ready-to-use form. A preferred concentrated form comprises about 40 percent fatty acid soap solution (50 percent monocarboxylic acids, a major amount of which is in alkali metal, preferably potassium, salt form), and 1.4 percent to about 5.6 percent by weight of a purified pyrethrum extract (20 percent by weight pyrethrins and other active extract substances) and 22 percent low molecular weight alcohol. Upon dilution about 20:1 with water, a ready-to-use solution results comprising about 1.0 percent fatty acid component and between about 0.01 percent and 0.014 percent active pyrethrum compounds.

In addition, the solution of the present invention is marketed in a dilute, ready-to-use formulation having the same percentages of fatty acid soap solution and pyrethrum extract as the dilute solution of the concentrate noted above. As marketed, the low molecular weight alcohol is present in an increased proportion, to about 5.6 percent by weight, to improve storage stability.

A third formulation of the solution of the present invention is marketed as a commercial concentrate wherein the fatty acid soap solution is present at about 80 percent by weight, the pyrethrum extract is present at about 2.8 percent by weight, and the low molecular weight alcohol is present at about 30 percent by weight.

The composition is manufactured by mixing together a solution of salts of fatty acids, water, an alcohol, an antioxidant, and the pyrethrum extract.

Domestic Concentrate

In the first preferred embodiment, the composition of the salts of fatty acids is an aqueous solution comprising about 50 percent by weight of a mixture of potassium salts of fatty acids and unneutralized fatty acids and about 30 percent by weight of ethanol. A suitable solution is available commercially from Safer, Inc. of Wellesley, Mass. under the trademark Safer Insecticidal Soap. The composition of this product varies slightly from batch to batch, but always includes at least about 70 percent salt (or acid form) oleic acid, and at least about 6 percent salt (or acid form) linoleic acid. The remainder of the solutes comprise other fatty acids or salts having between 12 and 20 carbon atoms. The fatty acid salt component is present in the concentrate at levels in the range of 10 to 50, preferably about 20, percent by weight.

The purified pyrethrum ether extract comprises about 20 percent by weight of a mixture of pyrethrin I and II, cinerin I and II, and jasmolin I and II. It is present in the concentrate at levels in the range of 0.05 to 5.6, preferably about 1.4, percent by weight. A suitable purified pyrethrum extract is commercially available from Fairfield American Corporation, Newark, N.J..

Other components of the concentrate include alcohol, preferably ethanol or isopropyl alcohol, which comprises between about 3 and 50 percent, preferably about 22 percent, by weight of the aqueous insecticide concentrate, and an effective amount, e.g., a trace amount, of an antioxidant, preferably a butylated hydroxytoluene, which constitutes approximately 0.02 percent by weight. The isopropyl alcohol can be purchased, for example, from Valley Products of Memphis, Tenn.. The butylated hydroxytoluene is available from, for example, Melville Synthetic Organics, Inc., of Pittsburgh, Pa.. The remainder of the insecticide concentrate constitutes diluents, primarily water, and inert ingredients introduced with the fatty acid and pyrethrum components.

The currently preferred embodiment of the domestic concentrate of the invention is made by mixing and gently agitating 100 parts Safer Insecticidal Soap (50 parts salts of fatty acids, 30 parts ethanol, and 20 parts water), 121.5 parts water, 25 parts isopropyl alcohol, 0.05 parts butylated hydroxytoluene, and 3.5 parts purified pyrethrum extract (20%). As formulated, the concentrate has a pH within the range of 7.5 to 8.8, preferably 8.0. This is diluted 20:1 with water before application to a plant.

Ready-to-Use Formulation

In the second preferred embodiment, the composition of the salts of fatty acids is an aqueous solution comprising about 50 percent by weight of a mixture of potassium salts of fatty acids and unneutralized fatty acids. The fatty acid salt component is present in the concentrate at levels in the range of 1 to 5, preferably about 1, percent by weight.

The purified pyrethrum ether extract comprises about 20 percent by weight of a mixture of pyrethrin I and II, cinerin I and II, and jasmolin I and II. It is present in the concentrate at levels in the range of 0.01 to 0.10, preferably about 0.07, percent by weight.

Other components of the concentrate include alcohol, which is preferably ethanol or isopropyl alcohol, which comprises between about 3 and 10 percent, preferably about 5.6 percent, by weight of the aqueous insecticide concentrate, and an effective amount, e.g., a trace amount, of an antioxidant, preferably a butylated hydroxytoluene, which constitutes approximately 0.001 percent by weight. The remainder of the insecticide concentrate constitutes diluents, primarily water, and inert ingredients introduced with the fatty acid and pyrethrum components.

The currently preferred embodiment of the ready-to-use formulation of the invention is made by mixing and gently agitating 100 parts Safer Insecticidal Soap (50 parts salts of fatty acids, 30 parts ethanol, and 20 parts water), 4646.5 parts water, 250 parts isopropyl alcohol, 0.05 parts butylated hydroxytoluene, and 3.5 parts purified pyrethrum extract (20%). As formulated, the concentrate has a pH within the range of 7.5 to 8.8, preferably 8.0.

Commercial Concentrate

In the third preferred embodiment, the composition of the salts of fatty acids is an aqueous solution comprising about 50 percent by weight of a mixture of potassium salts of fatty acids and unneutralized fatty acids. The fatty acid salt component is present in the concentrate at levels in the range of 10 to 50, preferably about 40, percent by weight.

The purified pyrethrum ether extract comprises about 20 percent by weight of a mixture of pyrethrin I and II, cinerin I and II, and jasmolin I and II. It is present in the concentrate at levels in the range of 2.0 to 4.0, preferably about 2.8, percent by weight.

Other components of the concentrate include alcohol, which is preferably ethanol or isopropyl alcohol, which comprises between about 3 and 50 percent, preferably about 30 percent, by weight of the aqueous insecticide concentrate, and an effective amount, e.g., a trace amount, of an antioxidant, preferably a butylated hydroxytoluene, which constitutes approximately 0.04 percent by weight. The remainder of the insecticide concentrate constitutes diluents, primarily water, and inert ingredients introduced with the fatty acid and pyrethrum components.

The currently preferred embodiment of the commercial concentrate of the invention is made by mixing and gently agitating 100 parts Safer Insecticidal Soap (50 parts salts of fatty acids, 30 parts ethanol, and 20 parts water), 11.16 parts water, 7.5 parts isopropyl alcohol, 0.05 parts butylated hydroxytoluene, and 3.5 parts purified pyrethrum extract (20%). As formulated, the concentrate has a pH within the range of 7.5 to 8.8, preferably 8.0. This is diluted 40:1 with water before application to a plant.

These formulations exhibit a combination of insecticidal activity, spectrum response, low vertebrate and phytotoxicity, and ready biodegradability unavailable in any composition known to applicants. Furthermore, unlike similar composition produced heretofor, both the concentrate and the ready-to-use solutions have commercially acceptable storage stability.

The following examples illustrate the lack of toxicity, efficacy, and storage stability of the insecticidal composition of the invention.

EXAMPLE 1

A highly concentrated form of an insecticide comprising fatty acid salts and pyrethrum extract was tested for animal toxicity. Rats were used for testing oral and inhalation toxicity, rabbits for dermal toxicity, rabbits in a Draize test for primary eye irritation and in a test for primary skin irritation, and guinea pigs for dermal sensitivity studies. The solution used comprised 40 percent Safer Insecticidal Soap and 0.4 percent pyrethrin (unless otherwise indicated below), a concentration approximating that of the preferred concentrate and about 20 times that of the ready-to-use solution. The following results indicate that the insecticide of the present invention, even in highly concentrated form, is substantially non-toxic to animals.

A. Oral $LD_{50}$ in Rats

Rats were fed various amounts of the concentrated insecticide, ranging up to 10.0 g/kg of body weight, in order to determine the oral $LD_{50}$, the dosage at which 50 percent of the rats died. No mortality of the rats occurred at this dose level and the testing was suspended.

B. Acute Dermal $LD_{50}$ in Rabbits

Rabbits were exposed to various amounts of the concentrated insecticide with the highest dosage being 2.0 g/kg of body weight, in order to determine a dermal $LD_{50}$. No mortality occurred among the rabbits at this dose level and essentially no symptoms of systemic toxicity were detected after day six or in postmortem examinations after a 2.0 g/kg body weight dermal application.

C. Acute Inhalation $LD_{50}$ in Rats

Rats were exposed to atmospheric concentrations up to 12.75 ml/l of the concentrated insecticide, of which 5.64 ml/l was respirable, to determine an inhalation $LD_{50}$. There was no mortality among the ten rats exposed over the entire fourteen day observation period.

D. Draize Test

The Draize test, see "Eye Irritation Testing", EPA-560 (11-82-001), published by the U.S. Environmental Protection Agency Office of Pesticides and Toxic Substances, was used to measure primary eye inflammation by contact with a concentrate comprising 20 percent Insecticidal Soap and 0.4 percent pyrethrin. This highly concentrated version of the insecticide was classified as a class three irritant after testing. When the eyes of the test animals were rinsed out twenty to thirty seconds after contact with the solution, there was essentially no irritation.

E. Primary Skin Irritation Test

Primary skin irritation studies using a 0.4 percent pyrethrum extract, 20 percent Insecticidal Soap mixture resulted in a finding of moderate to severe irritation, but essentially no irritation was observed at seven and nine days. In fact, the skin had returned to normal by day eight in all the test animals.

F. Dermal Sensitivity Studies

In dermal sensitivity studies using guinea pigs, the highly concentrated form of the insecticide was found to be very mildly sensitizing.

This Example illustrates that the insecticide of the invention, even in a highly concentrated form, has exceptionally low toxicity.

EXAMPLE 2

In this Example, a comparison of kill effectiveness was made between Insecticidal Soap without pyrethrum, the pyrethrum extract itself, and an insecticide comprising a combination of the two formulated in accordance with the ratio disclosed herein. The test involved applying the same amount of the sample to variegated cutworm and measuring mortality percentages. Table 1 shows the results of this experiment. As is obvious from the Table, the insecticide of the present invention does not show purely additive insecticidal properties with respect to this particular insect pest, but rather an unexpected, synergistic kill ratio.

TABLE 1

| Mixture | percent Mortality (Weight Ratio 50:1) | | | |
|---|---|---|---|---|
| | Neutral Soap | Pyrethrum | Expected | Observed |
| 0.1% Neutral Soap* 0.002% Pyrethrins | 2.8% | 31.4% | 34.2% | 65.7% |
| 0.05% Neutral Soap* 0.001% Pyrethrins | 8.6% | 20.0% | 28.6% | 45.7% |

*potassium oleate, neutralized with HCl, the most active component of Insecticidal Soap.

EXAMPLE 3

As previously noted, the insecticide of the invention has broad insecticidal activity. In order to demonstrate this activity, the insecticide was tested on a number of different species of insects. The results were compared with a positive control, MGK-7352, which contained 0.02 percent pyrethrins and piperonyl butoxide, and a negative control, distilled water. Table 2 lists a number of different insects and a mortality percentage obtained using the insecticide of the invention. SAP101 is a preferred form of the insecticidal solution of the invention, comprising 2 percent potassium Insecticidal Soap and 0.05 percent pyrethrum extract. Values in parentheses are duplicate runs of the same test.

TABLE 2

| INSECT | PERCENT MORTALITY | | | | | |
|---|---|---|---|---|---|---|
| | SAP101 | | MK7352 | | DISTILLED WATER | |
| Cabbage Aphids | 98.9 | (98.9) | 100.0 | (97.7) | 14.4 | (3.4) |
| Bean Aphid | 98.0 | (98.0) | 98.0 | | 12.0 | |
| Yellow Mealworm Adult | 75.0 | | 93.75 | | 0.0 | |
| Yellow Mealworm Larvae | 100.0 | | 50.0 | | 6.25 | |
| Milkweed Bug Larvae | 80.0 | | 72.5 | | 0.0 | |
| Milkweed Bug Adult | 100.0 | | 100.0 | | 6.7 | |
| Eastern Spruce Budworm | 100.0 | (95.0) | 100.0 | (100.0) | 0.0 | (2.5) |
| Imported Cabbage Worm | 100.0 | (97.5) | 100.0 | (100.0) | 0.0 | (0.0) |
| Cabbage Looper | | | | | | |

TABLE 2-continued

| INSECT | PERCENT MORTALITY | | |
|---|---|---|---|
| | SAP101 | MK7352 | DISTILLED WATER |
| Larvae | 100.0 | 100.0 | 2.0 |

As is exemplified by the results set forth in Table 2, the 2 percent IS/0.05 percent pyrethrum solution of the invention is effective in controlling a wide variety of insects. Other tests using different concentrations of soap and pyrethrins, still within the scope of the claims, have yielded similar results for a wide variety of insects.

EXAMPLE 4

To assess product stability, the pyrethrin content of both the domestic concentrate and the ready-to-use solution was measured after the test batches were freshly prepared, and again after normal and accelerated aging. Analyses were conducted in duplicate together with internal standards (di-n-butylphthalate) using gas/liquid chromatography.

On day one, a solution of ready-to-use product was prepared and placed in storage at room temperature in a brown glass bottle. The contents were sampled and analyzed four months later. The analyses resulted in a finding that 85.8 percent of the active pyrethrum content remained.

In another experiment, a sample of the domestic concentrate was stored in an oven at 50 degrees C. for 34 days. Upon analysis, it was determined that 86.1 percent of the pyrethrum active ingredients remained. When the experiment was repeated with a concentrate sample containing twice the normal (5.0%) isopropyl alcohol content, 74.2 percent of the pyrethrum active ingredients remained.

Two samples of ready-to-use solution were prepared, one containing a trace quantity of butylated hydroxytoluene (50 ppm), and one free of antioxidant. After accelerated aging in an oven at 50 degrees C. for 33 days, the former preparation was determined to contain 81.4 percent of the original pyrethrum active content. The sample containing no antioxidant was determined to contain no active pyrethrums.

Example 5

Experiments were conducted to evaluate the foliar and floral phytotoxicity of the insecticidal solution, as fatty acid salts have been observed to exhibit herbicidal activity. A representative number of vegetables, ornamental trees and shrubs, and floral plants were tested in a greenhouse. The plants were sprayed to run-off, and damage was assessed after 24 hours (for floral damage) and after 2–7 days (for foliar damage). The test samples were varied in pH, alcohol content, active fatty acid soap content, and pyrethrum content. As controls, a solution of 0.02 percent pyrethrins with piperonyl butoxide, and distilled water were used.

Foliar damage assessments were made using a 0–10 scale (0=healthy, 10=complete necrosis and death). A scale rating of 1 indicates that some damage occurred but was noticeable only on close inspection. A rating of 2 indicates damage which would be noticed on more casual inspection, but would involve less than 10 percent of the sprayed surface, and would be unlikely to involve permanent damage. A rating of 5 indicates 50 percent of the foliar surface is necrotic. Floral damage assessments were made using a 0–3 scale (0=healthy, 3=complete necrosis). Within this scale a 1 indicates some damage observed on close inspection, while a rating of 2 indicates unacceptable damage.

The results indicate that the ready-to-use product as formulated was characterized by only low, acceptable phytotoxicity toward all plant species tested, levels far below the piperonyl butoxide test preparations. Of the vegetables tested, only spinach showed a mean damage rating over 2. Preparations of lower pH generally were more phytotoxic. Of the ornamentals tested, only schizanthus showed unacceptable ratings of 2.67 ± 0.82. A ready-to-use formulation having a pH of 7.1 produced a damage rating of 4 on three sensitive species tested. No unacceptable rating were noted on trees or shrubs.

In the floral tests, among the plants tested, unacceptable damage occurred with a ready-to-use formulation only on rhododendron blooms. Severe damage also was observed with solutions formulated at pH 7.15 on some species. The ready-to-use product of the invention described above gave an acceptable rating of 1.3 ± 0.58.

In general, it was found that the solutions of the invention were far less phytotoxic than the butoxide-containing preparations. It also should be noted that phytotoxicity testing in the greenhouse is generally much more rigorous than the testing of field grown plants, which are generally healthier and hardier.

The foregoing Examples are purely illustrative and are not meant to limit the scope of the following claims.

What is claimed is:

1. A readily biodegradeable, environmentally safe, storage stabilized, aqueous, insecticidal solution for application to decorative and crop plants, said solution being effective to control plant damage from a wide range of chewing and sucking insects, said composition consisting essentially of:
    an aqueous solution having a pH between about 7.5 and 8.8 and containing the following ingredients in the following relative parts by weight:
    A. between 10 and 50 parts of a mixture of monocarboxylic acids and the alkali metal salts thereof, said monocarboxylic acids comprising at least 70 percent oleic acid and its alkali metal salts and at least 6 percent linoleic acid and its alkali metal salt;
    B. between 0.05 and 5.6 parts of a pyrethrum extract comprising about 20 percent by weight of a mixture of insecticidally active substances selected from the group consisting of pyrethrin I and II, cinerin I and II, and jasmolin I and II;
    C. between 3 and 225 parts of a low molecular weight alcohol; and
    D. a trace amount of an antioxidant,
    said composition being effective on application to a plant at a dilution in water such that the applied solution contains at least about 0.5 percent by weight of said monocarboxylic acid mixture and at least 0.005 percent by weight of said mixture of said insecticidally active pyrethrum extract substances to provide protection against plant damage from infestation by insect species from the orders Homoptera, Coleoptera, Dermaptera, Hemiptera, and Lepidoptera, and from crustacea species from the order Isopoda.

2. The solution of claim 1 wherein, on application, said solution is effective against species from the families Homoptera:Aphididae, Homoptera:Aleyrodidae, Homoptera:Coccidae, Homoptera:Psyllidae, Coleoptera:Chrysomelidae, Coleoptera:Tenebrionidae, Lepidoptera:Arctiidae, Lepidoptera:Lasiocampidae, Lepidoptera:Tortricidae, Lepidoptera:Pieridae, and Lepidoptera:Noctuidae.

3. The solution of claim 1 wherein the alkali metal salt is a potassium salt.

4. The solution of claim 1 wherein the relative ratio of ingredients A:B is about 20:1:4.

5. A concentrate of the solution of claim 1 for dilution with water to produce an insecticide suitable for spray application wherein ingredients A through D together comprise at least about 40 percent by weight of said solution.

6. The solution of claim 1 wherein said antioxidant is a hydroxylated aromatic compound.

7. The solution of claim 6 wherein said hydroxylated aromatic compound is butylated hydroxytoluene.

8. The solution of claim 1 wherein said alcohol has between 2 and 6 carbon atoms.

9. The solution of claim 8 wherein said alcohol is isopropyl alcohol.

10. The solution of claim 1 having a pH within the range of 8.0 to 8.5.

* * * * *